United States Patent [19]
Chatterjee et al.

[11] Patent Number: 5,441,727
[45] Date of Patent: Aug. 15, 1995

[54] DIKETONE DEODORANT COMPOSITION AND METHOD OF DEODORIZATION

[75] Inventors: Ranjit Chatterjee, Cincinnati; Rodney D. Bush, Fairfield, both of Ohio

[73] Assignee: The Procter & Gamble Company, Cincinnati, Ohio

[21] Appl. No.: 557,174

[22] Filed: Jul. 30, 1990

Related U.S. Application Data

[63] Continuation-in-part of Ser. No. 369,380, Jun. 21, 1989, abandoned.

[51] Int. Cl.$^6$ .................... A61K 7/32; B32B 3/00; C11D 3/48; C11D 9/50
[52] U.S. Cl. .................... 424/65; 252/106; 252/107; 424/66; 424/67; 424/68; 428/190; 428/227; 512/23; 514/844; 514/847; 514/937; 514/938
[58] Field of Search .................... 424/65; 512/23, 15

[56] References Cited

U.S. PATENT DOCUMENTS

| | | | |
|---|---|---|---|
| 3,172,817 | 3/1965 | Leupold et al. | 424/65 |
| 3,766,253 | 10/1973 | Cohen | 512/23 |
| 3,875,307 | 4/1975 | Wolt et al. | 512/23 |
| 4,126,641 | 11/1978 | Light et al. | 512/23 |
| 4,155,867 | 5/1979 | Hall et al. | 512/23 |
| 4,169,072 | 9/1979 | Hall et al. | 512/23 |
| 4,761,159 | 8/1988 | Knox | 604/49 |

FOREIGN PATENT DOCUMENTS

| | | | |
|---|---|---|---|
| 0126483 | 11/1984 | European Pat. Off. | 424/65 |
| 0147191 | 7/1985 | European Pat. Off. | 252/106 |
| 58-222010 | 12/1983 | Japan | 424/65 |
| 61-183206 | 8/1986 | Japan | 424/65 |
| 7315580 | 5/1974 | Netherlands | 512/23 |

OTHER PUBLICATIONS

Merck Index, 1976, 9th edition, pp. 420, 421 and 753.
Pharmaceutical Formulas, 1947, vol. II, pp. 150 and 151 and 152.
Johnson, B. C., T. S. Hamilton and H. H. Mitchell, "The Excretion of Pyridoxine, 'Pseudopyridoxine', and 4 Pyridoxic Acid in the Urine and Sweat of Normal Individuals", J. Biol. Chem., vol. 158 (1945), pp. 619–623.
Snell, E. E. "Non-Enzymatic Reactions of Pyridoxal and Their Significance", Chemical and Biological Aspects of Pyridoxal, Pergamon Press, Ltd., 1963, pp. 1–12.

*Primary Examiner*—Dale R. Ore
*Attorney, Agent, or Firm*—Milton B. Graff, IV; Brahm J. Corstanje; John M. Howell

[57] ABSTRACT

The present invention provides deodorant compositions for controlling malodor from perspiration comprising a safe an effective amount of a 1,3-diketone compound having the general formula:

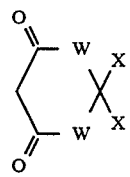

wherein each W is independently selected from the group consisting of O, S and $(CH_2)_n$, wherein $n = 1-3$; and each X is independently selected from the group consisting of hydrogen, halogen, substituted or unsubstituted alkyl having from about 1 to about 5 carbon atoms, or two X moieties are covalently bonded to form a substituted or unsubstituted alkyl, heteroalkyl, aryl or heteroaryl ring having from about 3 to about 12 atoms including from 0 to about 3 heteroatoms in the ring; and a topical carrier; whereby the composition is suitable for topical application to the skin or to articles of clothing worn in the vicinity of the skin.

Methods for controlling malodor comprising depositing on skin in the axilla or crotch region, or to articles of clothing worn in the vicinity of the skin of a safe and effective amount of a 1,3-diketone of the present invention, are also provided.

8 Claims, No Drawings

DIKETONE DEODORANT COMPOSITION AND METHOD OF DEODORIZATION

This application is a continuation-in-part of application Ser. No. 07/369,380, filed Jun. 21, 1989, now abandoned.

TECHNICAL FIELD

The present invention related to compositions and methods for the treatment or prevention of malodor associated with human perspiration.

BACKGROUND OF THE INVENTION

Vast volumes of the chemical, medical and cosmetic literature have been generated concerning the causes, effects and prevention of human perspiration. "Perspiration", or "sweat", may be generally defined as including the excretion of the sweat glands situated in the corium or subcutaneous tissue, known as eccrine sweat glands, distributed over most of the body surface. While perspiration serves an important function in cooling the body through its evaporation, the by-products resulting from its bacterial degradation may be malodorous and aesthetically objectionable.

Malodor is particularly associated with perspiration secreted at areas of the body where apocrine sweat glands, in addition to eccrine sweat glands, can be found. Two principal areas which have apocrine sweat glands are the axilla and the crotch. See, for example, J Labows, et al, "Perspectives on Axillary Odor" 34 *J. Soc. Cosmetic Chemists* 193-202 (1982) and P. Jackman, "Body Odor—The Role of Skin Bacteria" 1 *Seminars in Dermatology* 143-148 (1982). A variety of bacteria have been implicated in producing axillary malodor, a principal bacteria responsible for such malodor being the gram positive microflora naturally found in the axilla, e.g., the diphtheroids, such as the Corynebacteria and Propionibacteria, and the gram positive cocci, such as the Staphylococci and Micrococci.

A great number of compositions have been developed and described in the literature for reducing or eliminating the aesthetic problems associated with perspiration. See, for example, S. Plechner, "Antiperspirants and Deodorants", 2 *Cosmetics, Science and Technology*, 373-416 (M. Balsam and E. Sagarin ed. 1972). Such compositions can be generally classified as: antiperspirants, which serve to stop or reduce flow of perspiration; perfumes, which mask any objectionable odors resulting from perspiration; and deodorants, which stop or reduce the production of malodorous material in perspiration. For a variety of reasons, deodorant compositions are preferred by a large number of consumers. For example, some individuals are unable to use commercially-available antiperspirant products due to hypersensitivity to the astringent materials typically used in those products.

Deodorant compositions have primarily been thought of in the art in the context of stopping or reducing the formation of bacterial by-products in perspiration. This has been accomplished through the use of anti-microbial agents which attack the bacteria responsible for producing the malodorous by-products. While these anti-microbial deodorants have been effective in reducing malodor, they have not completely eliminated the formation of the malodorous condition. Thus, it is desirable to provide deodorant compositions which can further reduce malodor.

Additionally, it is desirable to reduce malodor once it is formed. In certain instances, malodor may remain, e.g., in the axilla and crotch areas, or in axilla and crotch areas of articles of clothing, even after washing. Traditionally, malodor that is already formed has been masked by perfumes. It is desirable to provide improved methods and compositions for reducing malodor that can remain subsequent to washing of the person or articles of clothing. In one approach, described in PCT International Patent Application Publication Number WO 87/04341, published Jul. 30, 1987, it is disclosed that axillary malodor can be neutralized by the use of cupric sulfate, silver sulfate, potassium permanganate, ferric chloride, sodium hydroxide, silver proteinate, sodium hypochlorite, zinc sulfate, or copper gluconate. However, it is desirable to provide alternative technology for neutralizing malodor.

It is an object of this invention to provide compositions effective for controlling nonmicrobial malodor from human sweat. It is a further object of this invention to provide methods effective for controlling malodor from human sweat.

SUMMARY OF THE INVENTION

The present invention provides deodorant compositions for controlling malodor from perspiration comprising a safe an effective amount of a 1,3-diketone compound having the general formula:

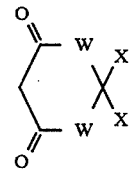

wherein each W is independently selected from the group consisting of O, S and $(CH_2)_n$ wherein $n=1-3$; and each X is independently selected from the group consisting of hydrogen, halogen, substituted or unsubstituted alkyl having from about 1 to about 5 carbon atoms or two X moieties are covalently bonded to form a substituted or unsubstituted alkyl or aryl ring having from about 3 to about 12 carbon atoms in the ring; and a topical carrier for topical application to the skin or to articles of clothing worn in the vicinity of the skin. Methods for controlling malodor from perspiration comprising topically applying to skin in the axilla or crotch region of a safe and effective amount of the 1, 3-diketone compounds or compositions of the present invention, are also provided. Laundry product, fabric treatment, diaper and catamenial compositions comprising such 1,3-diketone compounds are also included in the present invention.

DETAILED DESCRIPTION OF THE INVENTION

Although it has been suggested that malodor formation and neutralization may involve more than one mechanism, such mechanisms are not completely understood. Applicants have determined that when perspiration from the axilla or crotch areas of humans is sterilized such that substantially no live bacteria remain to produce malodorous bacterial by-products, the perspiration still develops aesthetically objectionable malodor. Such malodor shall hereinafter be referred to as "nonmicrobial malodor". Applicants have determined that certain vitamin B6 compounds commonly secreted by humans from their eccrine sweat glands can react when mixed with apocrine sweat gland secretions to form nonmicrobial malodor. Applicants have further determined that deodorant compositions containing certain 1,3-diketone compounds are highly effective for reducing such nonmicrobial malodor in human perspiration. These compositions are particularly useful for controlling malodor in perspiration containing both apocrine and eccrine sweat. Furthermore, such compositions are effective for preventing the formation of nonmicrobial malodor.

The 1,3-diketone compositions of the type described above have been found to be highly effective for inhibiting the occurrence of the malodorous condition of perspiration and, further, for deodorizing malodorous perspiration or preventing formation of malodor in perspiration. Nonmicrobial malodor increases over time, especially when the rate of perspiration is high and when the time between washing is extended. It is believed that the concentration of nonmicrobial malodor precursors on the skin increases as additional perspiration is secreted and the aqueous component of previously secreted perspiration evaporates, thus increasing the formation of discernible nonmicrobial malodor. Without being limited by any theory, it is believed that 1,3-diketone compounds react with the aldehyde from of vitamin B6 (PLP) by acting as strong nucleophiles at the Z-carbon site between the ketone groups, altering the PLP molecule, and preventing its combination with other compounds in sweat that normally leads to the formation of malodor. The occurrence of such malodorous conditions from nonmicrobial sources can be substantially diminished by the 1,3-diketone compounds and compositions of the present invention.

The compositions of the present invention comprise, as essential components, a 1,3-diketone compound for controlling nonmicrobial malodor and a compatible carrier. As used herein, "controlling nonmicrobial malodor" means reducing previously formed nonmicrobial malodor to a less perceptible level to the human olfactory senses and/or inhibiting the occurrence of a nonmicrobial malodor. As used herein, "compatible" means that none of the components of the carrier reacts with the 1,3-diketone compound such that the ability of the composition to control nonmicrobial malodor is substantially impaired.

The term "alkyl", as used herein, means carbon-containing chains that are straight, branched, or cyclic; and which are saturated or monounsaturated (i.e. one double or triple bond in the chain) or polyunsaturated (e.g. two or more double bonds in the chain; two or more triple bonds in the chain; one or more double and one or more triple bonds in the chain) and which are substituted or unsubstituted. As used herein, saturated alkyl groups are referred to as "alkanyl"; unsaturated alkyl groups comprising double bonds in the chain are referred to as "alkenyl"; and unsaturated alkyl groups comprising triple bonds in the chain are referred to as "alkynyl". The term "short chain alkyl", as used herein, means alkyls having from 1 to about 6 carbon atoms in the chain.

The term "aryl", as used herein, means aryl radicals which are substituted or unsubstituted. "Substituted aryl" means aryl radicals which have substituents on the aryl ring. Examples of aryls include phenyl, napthyl, and substituted phenyl or napthyl.

The term "substituted", as used herein means mono- or polysubstituted, especially mono-, di- or trisubstituted. Examples of substitutents include halogen (especially fluorine, chlorine or bromine), alkyl, hydroxy, amino, aryl (especially phenyl or napthyl), carboxylate, nitro, and —$CF_3$, or —OR wherein R is an unsubstituted alkyl group having from about 1 to about 3 carbon atoms (especially methoxy and ethoxy). Alkyl substituents are preferably $C_1$-$C_6$ alkyl, more preferably $C_1$-$C_6$ alkanyl; even more preferably methyl or ethyl.

The deodorant agents of the present invention are cyclic diketone compounds having the general formula:

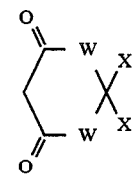

wherein each W is independently selected from the group consisting of O, S and $(CH_2)_n$, wherein n=1−3; and each X is independently selected from the group consisting of hydrogen, halogen, substituted or unsubstituted alkyl having from about 1 to about 5 carbon atoms, or two X moieties are covalently bonded to form a substituted or unsubstituted alkyl, heteroalkyl, aryl or heteroaryl ring having from about 3 to about 12 atoms in the ring including from 0 to about 3 (preferably 0 or 1) heteroatoms. As used herein, "heteroatoms" means atoms which will covalently bond to two other atoms to form stable rings. Preferred heteroatoms include N, O and S.

Preferred W is independently selected from the group consisting of O or $(CH_2)_n$ wherein n=1−3. More preferred is when both W are O or when one W is O and one W is $(CH_2)_n$ wherein n=1−3; also more preferred is when both W are $(CH_2)_n$ wherein n=1−3; even more preferred is when both W are O or one W is O and one W is $CH_2$; also even more preferred is when both W are $CH_2$. Most preferred is when both W are O.

X is preferably independently selected from the group consisting of hydrogen, halogen (especially chloro or fluoro), and substituted or unsubstituted alkyl having from about 1 to about 5 carbon atoms or two X moieties are covalently bonded to form a substituted or unsubstituted alkyl or aryl ring having from about 5 to about 6 carbon atoms. Preferably such ring is alkanyl, alkenyl or phenyl, preferably unsubstituted. More preferred X is independently selected from the group consisting of hydrogen and substituted or unsubstituted alkanyl or alkenyl having from about 1 to about 5 carbon atoms; even more preferred X is independently selected from the group consisting of hydrogen and unsubstituted or substituted alkanyl (especially hydroxymethyl). Even further preferred is one X being hydrogen, the other X being unsubstituted or substituted alkanyl having from about 1 to about 5 carbon atoms. Also even further preferred is X being independently selected from the group consisting of hydrogen, methyl or ethyl. Most preferred is both X being methyl.

Compositions of the present invention preferrably comprise 1,3-diketone compounds selected from the group consisting of 5,5-dimethyl-1,3-cyclohexanedione (dimedone), 2,2-dimethyl-1,3-dioxane-4,6-dione (Meldrum's acid), spiro-[4.5]-6,10-dioxa-7,9-dioxodecane, spiro-[5.5]-1,5-dioxa-2,4-dioxoundecane, 2,2-hydroxymethyl-1,3-dioxane-4,6-dione and 1,3-cyclohexadione. More preferred are spiro [4.5]-6,10-dioxa-7,g-dioxodecane, spiro [5.5]-1,5-dioxa-2,4-dioxoundecane, and 2,2-hydroxymethyl-1,3-dioxane-4,6-dione. Most preferred is 2,2-dimethyl-1,3-dioxane-4,6-dione.

Substituted moieties are limited to those which do not cause the compound to become substantially malodorous or ineffective for controlling malodor. Additionally, it is preferable that W, X and substituents of the 1,3-diketone compounds be limited such that they do not react with components generally found in perspiration to form discernibly malodorous substances, or such that the 1,3-diketone compounds would be unavailable to react with the vitamin $B_6$ aldehyde compounds in the perspiration. However, perfumes can be added to the compositions, as optional ingredients, to mask slight malodors of the 1,3-diketone compound and its reaction products.

The compositions of the present invention comprise a safe and effective amount of a 1,3-diketone compound when used as intended. As used herein, a "safe and effective amount" is an amount which is effective for eliminating or substantially reducing nonmicrobial malodor, while being safe for the intended use at a reasonable benefit/risk ratio.

1,3-diketone compounds useful in the compositions of the present invention can be obtained commercially from industry chemical sources, such as Sigma Chemical Company (St. Louis, Miss.), Aldrich Chemical Company (Milwaukee, Wis.), K&K Laboratories (Plainview, N.Y.), and P&B Research Chemicals (Waterbury, Conn.).

A. Topical Compositions

One aspect of the present invention is deodorant compositions which comprise a 1,3-diketone compound and a topical carrier. The deodorant compositions of the present invention comprising a 1,3-diketone compound can be a variety of products which, in ordinary use, are applied topically to the skin or are applied to articles of clothing which are worn in the vicinity of the skin. Compositions formulated for topical application to skin, or prepared for deposition upon articles of clothing and intended to at least initially remain deposited at the time that the article is worn, comprise a safe and effective amount of the 1,3-diketone compound and a topical carrier for depositing or releasing the deodorant agent. As used herein "applied to the skin" and "application to the skin" include deposit on the skin such that the deodorant agent can remain on the skin subsequent to the typical use of the composition as well as treatment of the skin with the composition wherein the deodorant agent is typically not deposited, e.g., skin cleaning compositions (discussed in more detail below) which are typically rinsed off subsequent to use.

The topical carriers of the deodorant compositions of the present invention can be in the form of liquids, solids, creams, gels, lotions, or other forms, and are preferably formulated to deposit the deodorant agent on the skin or article of clothing. As used herein, "deposited" and "deposit" of the deodorant agent on the skin means application of a deodorant composition to the skin such that the deodorant agent can remain on the skin subsequent to the typical use of the deodorant composition, including conventional post-deodorant composition application steps, if any. Such topical carriers include, but are not limited to, those formulated as conventional deodorant compositions such as creams, sticks, roll-on liquids and spray liquids (including aerosols); body lotions, creams and oils, such as skin lotions, skin conditioners, sun and wind screens, and sun tanning lotions and oils; and skin cleansing products such as bar soaps, liquid soaps and cleaning gels.

Typically, topical deodorant compositions of the present invention contain from about 0.01% to about 20% of the 1,3-diketone deodorant agent, preferably from about 0.05% to about 5%, more preferably from about 0.5% to about 2%.

Preferred deodorant compositions of the present invention are conventional deodorant compositions, including anti-perspirant/deodorant compositions, formulated for topical application to the axilla area of the body, or for application to the crotch area. The specific components to be included in the deodorant compositions of the present invention depend upon the particular mode of application that is desired. These methods of application, as well as the components that may be used in such compositions are well known in the art. Many such compositions are described in S. Plechner, "Antiperspirants and Deodorants" 2 *Cosmetics, Science and Technology*, 373–416 (M. Balsam and E. Sagarin ed. 1972), incorporated by reference herein.

A topical carrier for deodorant compositions formulated primarily for deposit of the 1,3-diketone deodorant agent on the skin in the axilla area for malodor control is preferably hydrophobic, with less than about 5% water, more preferably less than about 2% water, and most preferably with essentially zero percent water. Other compositions may contain high amounts of water, for the presence of water is not believed to affect the efficacy of the 1,3-diketone deodorant agent.

Topical carriers useful for depositing the 1,3-diketone deodorant agents to skin in the form of creams, ointments, lotions, oil-in-water and water-in-oil emulsions are known in the art, and include, for example, the water-in-oil emulsions disclosed in U.S. Pat. No. 4,254,105, Fakuda et al., issued Mar. 3, 1981 (incorporated by reference herein), and triple emulsion carrier systems such as the oil-in-water-in-silicone fluid emulsions as disclosed in European Patent Specification 281,394, Figueroa et al., published Sep. 7, 1988 (incorporated by reference herein).

1. Liquids

Liquid compositions useful herein, such as roll-ons, sprays, and aerosols, preferably contain a liquid emollient as all or a substantial part of the topical carrier. Such compositions are suitable for delivery (respectively) from conventional roll-on, spray and aerosol containers known in the art. Such emollients include fatty acid and fatty alcohol esters, water-insoluble ethers and alcohols, polyorganosilicones, and mixtures thereof. Polyorganosilicones are among the preferred emollients useful herein. Liquid topical carriers are disclosed in the following patent documents, incorporated by reference herein: U.S. Pat. No. 4,053,851, Pader, et al., Oct. 11, 1977; U.S. Pat. No. 4,065,564, Miles, Jr., et al., issued Dec. 27, 1977; U.S. Pat. No. 4,073,880, Pader, et al., issued Feb. 14, 1978; U.S. Pat. No. 4,278,655, Elmi, issued Jul. 14, 1981; British Patent Application 2,018,590, Elmi, et al., published Oct. 24, 1979; and European Patent Specification 28,853, Beckmeyer, et al., issued Jul. 11, 1984.

The liquid deodorant compositions of the present invention may also contain an alcohol and/or a polyol as a substantial component in the topical carrier. Alcohols useful herein include ethanol, propanol, isopropanol, and mixtures thereof. Polyols useful herein include glycols such as propylene glycol.

The present liquid compositions may also contain a bulking agent to modify the physical and/or cosmetic characteristics of the composition. Such bulking agents are typically present at a level of from about 1% to about 8%. Bulking agents useful herein include talc, colloidal silicas, clays, and mixtures thereof.

2. Aerosols

Aersol compositions of the present invention contain one or more volatile materials, herein "aerosol propellants", which in a gaseous state carry the other components of the present invention. The aerosol propellants useful herein typically have a boiling point within the range of from about $-45°$ C. to about $5°$ C. The aerosol propellants are liquified when packaged in conventional aerosol containers under pressure. The rapid boiling of the aerosol propellant upon leaving the aerosol container aids in the atomization of the other components of the aerosol compositions.

Aerosol propellants useful herein include those well known in the art. Such aerosol propellants include the chemically-inert hydrocarbons such as propane, n-butane, isobutane, cyclopropane and mixtures thereof, as well as halogenated hydrocarbons such as dichloro difluoromethane (propellant 12), 1,1-dichlor-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), monochlorodifluoromethane, and mixtures thereof. Isobutane, used singly or admixed with other hydrocarbons, is preferred for use in aerosol compositions of the present invention.

3. Deodorant Sticks

Solid compositions of the present invention, as in a stick form known in the art, typically comprise a liquid base material and a solidifying agent. These deodorant sticks can generally be described as being either gel sticks or wax sticks, depending upon the particular liquid base materials and solidifying agents used. In general, liquid base materials are present at a level of from about 10% to about 97%. The solidifying agent is typically present at a level of from about 1% to about 7%.

As is appreciated by those skilled in the art, the selection of a particular liquid base material, as well as the selection of a suitable solidifying agent, will vary depending upon the particular type and theology of deodorant stick desired. A variety of liquid base materials and solidifying agents among those useful herein, as well as sticks made from these materials, are described in the following documents, all incorporated by reference herein: S. Plechner, "Antiperspirants and Deodorants", 2 *Cosmetics, Science and Technology*, 373–416 (M. Balsam and E. Sagarin ed. 1972); C. Fox "Gel and Sticks Review and Update", 99 *Cosmetics & Toiletries* 19–52 (1984); N. Geria, "Formulation of Stick Antiperspirants and Deodorants", 99 *Cosmetics & Toiletries*, 55–99 (1984); and "Gels and Sticks Formulary", 99 *Cosmetics & Toiletries*, 77–87 (1984).

The liquid base materials used in wax deodorant sticks generally also serve as emollients, improving the cosmetic acceptability of the deodorant sticks. Such emollient materials include fatty acid and fatty alcohol esters, water-insoluble ethers and alcohols, polyorganosiloxanes, and mixtures thereof. Polyorganosiloxanes are among the preferred liquid base materials useful in wax deodorant sticks of the present invention.

Solidifying agents useful in wax deodorant sticks of the present invention are waxy materials typically incorporated at a level of from about 5% to about 50%. Among such waxy materials useful herein are the high melting point waxes, having a melting point of from about 65° C. to 102° C. Lower melting point waxes having a melting point of from about 37° C. to 75° C. are preferred. Such low-melting point waxes include fatty acids, fatty alcohols, fatty acid esters and fatty acid amides, and mixtures thereof. Stearyl alcohol, cetyl alcohol, and mixtures thereof are among the particularly preferred waxy materials useful in the deodorant stick compositions of the present invention. Liquid base materials and solidifying agents among those useful in the wax-type deodorant sticks of this invention are disclosed in the following U.S. Patents, incorporated by reference herein: U.S. Pat. No. 4,049,792, Elsnau, issued Sep. 20, 1977; U.S. Pat. No. 4,151,272, Geary, et al., issued Apr. 24, 1979; U.S. Pat. No. 4,299,432, Geria, issued Oct. 21, 1980; U.S. Pat. No. 4,280,994, Turney, issued Jul. 28, 1981; U.S. Pat. No. 4,126,679, Davy, et al., issued Nov. 21, 1978; and European Patent Specification 117,070, May, published Aug. 29, 1984.

Gel deodorant sticks of the present invention contain liquid base material which may be selected so as to also provide desirable cosmetics, such as emolliency and/or a cooling sensation when applied to the skin. Liquid base materials useful in such gel sticks include water, lower monohydric alcohols, polyhydric alcohols, and mixtures thereof. Among such materials are ethanol, isopropanol, n-propanol, n-butanol, i-butanol, t-butanol, ethylene glycol, propylene glycol, trimethylene glycol, glycerine, 1,3-butanediol, 1,4-butanediol, and mixtures thereof. Ethanol, propylene glycol, and mixtures thereof are preferred liquid base materials for use in gel sticks of this invention.

Solidifying agents useful in gel deodorant sticks of this invention are, in general, surface-active compounds which form networks irammobilizing or solidifying the liquid base materials into a gel. Such solidifying agents typically include soaps, higher fatty acid amides of alkyl amines, benzylidene sorbitols, propionates and lactates, waxes, and mixtures thereof. Preferable solidifying agents in gel deodorant sticks of the present invention are nonionic in character. Among the preferred solidifying agents useful in the gel deodorant sticks of this invention are the benzylidene sorbitols, in particular the dibenzaldehyde monosorbitol acetals. Such materials are available from a variety of sources, e.g., Gell All-De (manufactured by New Japan Chemical Company, Ltd.) and Millithixs (Manufactured by Nilliken Chemical, Division of Milliken & Company). Liquid base materials and solidifying agents among those useful in the gel-type deodorant sticks of this invention are disclosed in the following patent documents, all incorporated by reference herein: U.S. Pat. No. 2,900,306, Slater, issued Aug. 18, 1959; U.S. Pat. No. 3,255,082, Barton, issued Jun. 7, 1966; U.S. Pat. No. 4,137,306, Rubino, et al., issued Jan. 30, 1979; U.S. Pat. No. 4,154,816, Roehl, et al., issued May 15, 1979; U.S. Pat. No. 4,226,889, Yuhas, issued Oct. 7, 1980; U.S. Pat. No. 4,346,079, Roehl, issued Aug. 24, 1982; U.S. Pat. No. 4,383,988, Teng, et al., issued May 17, 1983; U.S. Pat. No. 4,504,465, Sampson et al., issued Mar. 12, 1985; and European Patent Specification 107,330, Luebbe, et al., published May 2, 1984; and U.S. Pat. No. 4,816,261, Luebbe et al, issued 1989. Preferred gel sticks, incorporating benzylidene sorbitols and cetyl alcohol, are described in U.S. Pat. No. 4,743,444, McCall, issued May 10, 1988 (incorporated by reference herein).

The deodorant sticks of the present invention, particularly the wax-type deodorant sticks, may contain inert filler materials. Such materials include talc, colloidal silica (such as Cab-O-Sil®, sold by Cabot Corporation), clays (such as bentonites) and mixtures thereof. Such filler materials are described in U.S. Pat. No. 4,126,679, Davy, et al., issued Nov. 21, 1978 (incorporated by reference herein) and European Patent Specification 117,070, May, published Aug. 29, 1984 (incorporated by reference herein).

The deodorant compositions of the present invention for topical application to skin may also contain optional components which serve as additional "active" components when deposited on the skin in addition to the 1,3-diketone deodorant agents of the present invention. Such additional active components preferably do not, however, substantially interfere with the deodorant activity of 1,3-diketone. Active components include, but are not limited to, other deodorant agents, such as anti-microbial agents, e.g. bacteriocides and fungicides, and antiperspirant agents. The active components must be stable in the formulations of the present compositions. A "safe and effective" amount of an active component is preferably used. Various active components among those useful in this invention are described in U.S. Pat. No. 4,226,889, Yuhas, issued Oct. 7, 1980 (incorporated by reference herein) and include, but are not limited to, 2,2'-methylene-bis(3,4,6-trichlorophenol), zinc phenolsulfonate, 2,2'-thiobis(4,6-dichlorophenol), p-chloro-m-xylenol, and dichloro-m-xyleno.

Preferred antiperspirant materials useful in the deodorant compositions of this invention include aluminum and zirconium salts, such as aluminum halides, aluminum hydroxy halides, zirconyl oxide halides, zirconyl hydroxy halides, and mixtures thereof. Antiperspirant materials among those useful herein are described in European Patent Specification 28,853, Beckmeyer, et al., published Jul. 11, 1984 (incorporated by reference herein). Such materials are typically included at levels of from about 15% to about 40%; based upon the total weight of the composition.

Other optional antiperspirant materials include antihistamines selected from the group of ethanolamines, ethylenediamines, alkylamines, phenothiazines, and piperazines, or pharmaceutically acceptable salts thereof, as described in U.S. Pat. No. 4,226,850, Packman, issued Oct. 7, 1980 and U.S. Pat. No. 4,234,566, Packman, issued Nov. 18, 1980 (both incorporated by reference herein). Still other optional antiperspirant materials include various anticholinergic agents, such as esters of the Belladonna alkaloids scopolamine and atropine, as disclosed in U.S. Pat. No. 3,312,709, MacMillan, issued Apr. 4, 1967, U.S. Pat. No. 3,326,768, MacMillan, issued Jun. 20, 1967, U.S. Pat. No. 3,767,786, MacMillan, issued Oct. 23, 1973, and U.S. Pat. No. 3,624,200, Moffett, issued Nov. 1971 (all incorporated by reference herein).

As is appreciated by those skilled in the art, certain of the antiperspirant materials described above may be ineffective in, or lead to instability of, compositions of this invention. Accordingly, compositions of this invention may contain a buffering agent so as to maintain a pH of at least about 6.0 in the composition. Such buffering agents are described in U.S. Pat. No. 4,154,816, Roehl, et al., issued May 15, 1979, U.S. Pat. No. 4,346,079, Roehl, issued Aug. 24, 1982; and U.S. Pat. No. 4,518,582, Schamper, et al., issued May 21, 1985 (all incorporated by reference herein).

Among the preferred compositions of the present invention are those which also include a safe and effective amount of deodorant agents other than the 1,3-diketone deodorant agent, such as antimicrobial agents (e.g. bacteriocides and fungicides), or mixtures thereof. Such other deodorant agents are usually present at levels of from about 0.1% to 10% (by weight of the composition). Suitable other deodorant agents include bacteriostatic quaternary ammonium compounds such as cetyltrimethyl ammonium bromide, cetyl pyridinium chloride, benzethonium chloride, diisobutyl phenoxy ethoxy ethyl dimethyl benzyl ammonium chloride, sodium N-lauryl-sarcosine, sodium N-polymethyl sarcosine, lauroyl sarcosine, N-myristoyl glycine, potassium N-lauroyl sarcosine, stearyl trimethyl ammonium chloride, and mixtures thereof. Other suitable deodorant agents include 2,4,4'-trichloro-2'hydroxydiphenyl ether, zinc pyrithione (ZPT), and sodium bicarbonate. Particularly preferred other deodorant agents include a diaminoalkyl amide, such as L-lysine hexadecyl amide, as disclosed in U.S. Pat. No. 3,574,747, Denning, issued Apr. 13, 1971 (incorporated by reference herein).

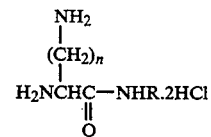

Other optional components of the deodorant compositions of the present invention include perfumes, pigments, dyes, colorants, and ultraviolet absorbers.

The deodorant compositions of the present invention may be made by a variety of techniques well know in the art. For example, such techniques for making solid deodorant compositions are described in "Gels and Sticks Formulary", 99 *Cosmetics & Toiletries* 77–87 (1984), incorporated by reference herein.

4. Creams, Ointments and Lotions

Creams, ointments, and lotion composition of the present invention typically comprise one or more emollients as components of the topical carriers. As used herein, "emollients" refer to materials used for the prevention or relief of dryness, as well as for the protection of the skin. A wide variety of suitable emollients are known and may be used herein. Sagatin, *Cosmetics, Science and Technology,* 2nd Edition, Vol. 1, pp. 32–43 (1972), incorporated herein by reference, contains numerous examples of suitable materials. Examples of classes of useful emollients include the following:

Hydrocarbon oils and waxes; silicone oils, such as dimethyl polysiloxanes, methylphenyl polysiloxanes, water-soluble and alcohol-soluble silicone glycol copolymers; triglyceride esters, for example vegetable and animal fats and oils; acetoglyceride esters, such as acetylated monoglycerides; ethoxylated glycerides, such as ethoxylated glyceryl monostearate; alkyl esters of fatty acids having 10 to 20 carbon atoms; alkenyl esters of fatty acids having 10 to 20 carbon atoms; fatty acids having 10 to 20 carbon atoms; fatty alcohols having 10 to 20 carbon atoms; fatty alcohol ethers; ether-esters such as fatty acid esters of ethoxylated fatty alcohols; lanolin and derivatives; polyhydric alcohols and polyether derivatives; polyhydric alcohol esters; wax esters such as beeswax, spermaceti, myristyl myristate, stearyl stearate; beeswax derivatives; vegetable waxes including carnauba and candelilla waxes; phospholipids, such as lecithin and derivatives; sterols such as cholesterol and cholesterol fatty acid esters; and amides such as fatty acid amides, ethoxylated fatty acid amides, solid fatty acid alkanolamides.

Particularly useful emollients which provide skin conditioning are glycerol, hexanetriol, butanetriol, lactic acid and its salts, urea, pyrrolidone carboxylic acid and its salts, amino acids, guanidine, diglycerol and triglycerol.

A lotion of the present invention in the form of a solution typically comprises from about 0.01% to about 20%, preferably from about 0.1% to about )5%, of a 1,3-diketone deodorant agent; from about 1% to about 20%, preferably from about 5% to about 10%, of an emollient; and from about 50% to about 90%, preferably from about 60% to about 80%, water. A cream of the present invention in the form of a solution typically comprises from about 0.01% to about 20%, preferably from about 0.1% to about 5%, of a 1,3-di ketone deodorant agent; from about 5% to about 50%, preferably from about 10% to about 20%, of an emollient, and from about 45% to about 85%, preferably from about 50% to about 75%, water.

An ointment of the present invention may comprise a simple base of animal or vegetable oils or semi-solid hydrocarbons (oleaginous). Ointments may also comprise absorption ointment bases which absorb water to form emulsions. Examples of such ointment bases include anhydrous lanolin and hydrophilic petrolatum. Emulsion ointment bases may be oil-in-water or water-in-oil emulsions. Ointment carriers may also be water soluble. Examples of such ointment carriers include components such as glycolethers, propylene glycols, polyoxyl stearates, and polysorbates. An ointment typically comprises from about 2% to about 10% of an emollient plus from about 0.1% to about 2% of a thickening agent. A more complete disclosure of thickening agents useful herein can be found in Segarin, *Cosmetics, Science and Technology*, 2nd Edition, Vol. 1, pp. 72–73 (1972), incorporated herein by reference.

If a topical carrier of the present invention is formulated as an emulsion, typically from about 1% to about 10%, preferably from about 2% to about 5%, of the carrier comprises an emulsifier. Emulsifiers may be nonionic, anionic or cationic. Suitable emulsifiers are disclosed in, for example, U.S. Pat. No. 3,755,560, issued Aug. 28, 1973, Dickert et al,; U.S. Pat. No. 4,421,769, issued Dec. 20, 1983, Dixon et al.; and McCutcheon's *Detergents and Emulsifiers*, North American Edition, pages 317–324 (1986); the disclosures of which are incorporated herein by reference. Preferred emulsifiers are anionic or nonionic, although the other types may also be used.

Single emulsion skin care preparations, such as lotions and creams, of the oil-in-water type and water-in-oil type are well-known in the cosmetic art and are useful in the present invention. Multiphase emulsion compositions, such as the water-in-oil-in-water type, as disclosed in U.S. Pat. No. 4,254,105, Fakuda et al., issued Mar. 3, 1981, herein incorporated by reference, are also useful in the present invention. In general, such single or multiphase emulsions contain water, emollients and emulsifiers as essential ingredients.

Triple emulsion carriers comprising an oil-in-water-in-silicone fluid emulsion composition as disclosed in European Patent Specification 281,394 (supra) are also useful in the present invention. More particularly, such triple emulsion carrier systems comprise a) from about 15% to about 90% by weight (of the vehicle) of a silicone fluid continuous phase consisting essentially of at least one liquid organopolysiloxane, b) from about 30% to about 80% by weight (of the vehicle) of an aqueous discontinuous phase comprising an oil-in-water emulsion of a cosmetically-acceptable oily liquid non-particulate phase dispersed in an aqueous phase and c) from about 0.5% to about 5% by weight (of the vehicle) of an effective dispersing amount of dimethicone copolyol for dispersing (b) in (a).

Another emulsion carrier useful in the compositions of the present invention is a micro-emulsion carrier. Such a carrier comprises from about 9% to about 15% squalane; from about 25% to about 40% silicone oil; from about 8% to about 20% of a fatty alcohol; from about 15% to about 30% of polyoxyethylene sorbitan mono-fatty acid (commercially available under the trade name Tweens®) or other nonionics; and from about 7% to about 20% water.

Lotions and creams can be formulated as emulsions as well as solutions. Typically such lotions in the form of emulsions comprise from about 0.01% to about 20%, preferably from about 0.1% to about 5%, of a 1,3-diketone deodorant agent from about 1% to about 20%, preferably from about 5% to about 10%, of an emollient; from about 25% to about 75%, .preferably from about 45% to about 95%, water; and from about 1% to about 10%, preferably from about 2% to about 5%, of an emulsifier. Such creams in the form of emulsions typically comprise from about 0.01% to about 20%, preferably from about 0.1% to about 5%, of a 1,3-diketone deodorant agent; from about 1% to about 20%, preferably from about 5% to about 10%, of an emollient; from about 20% to about 80%, preferably from about 30% to about 70%, water; and from about 1% to about 10%, preferably from about 2% to about 5%, of an emulsifier.

5. Skin Cleansing

In addition to the deodorant compositions described above, the deodorant compositions of the present invention include skin cleansing deodorant compositions, which comprise a 1,3-diketone compound and a topical carrier which includes a safe and effective surfactant for topical application to human skin. The term "safe and effective surfactant for topical application to human skin" refers to a surfactant which is not only an effective skin cleanser, but also can be used without undue toxicity, irritation, allergic response, and the like. The skin cleansing deodorant compositions of the present invention preferably contain from about 0.01% to about 20% of the 1,3-diketone deodorant agent and from about 1% to about 90%, preferably from about 50% to about 90%, of a surfactant for topical application to human skin.

The physical form of the skin cleansing, deodorant compositions is not critical. The compositions can be, for example, formulated as toilet bars, liquids, pastes, or mousses. Toilet bars are most preferred since this is the form of cleansing agent most commonly used to wash the skin.

Those skilled in the art will recognize that active ingredients applied to skin from skin cleansing compositions may not significantly deposit on the skin due to factors such as rinsing which typically follows the application of such products. Even when significant deposit of the 1,3-diketone on the skin is not attained, the compositions can still be highly effective for controlling nonmicrobial malodor that was previously formed in the axilla or crotch areas. Controlling nonmicrobial malodor in connection with skin cleaning compositions is especially of great benefit since malodorous skin condition can remain even after the affected axilla and crotch areas are washed with conventional skin cleansing compositions.

Any safe and effective surfactant which is compatible with the 1,3-diketone deodorant agent can be used in the compositions of the present invention, including surfactants selected from anionic, nonionic, zwitterionic, amphoteric and ampholytic surfactants, as well as mixtures of these surfactants. Such surfactants are well-known to those skilled in the detergency art. Suitable surfactants can be found, for example, in McCutcheon's *Detergents and Emulsifiers*, North American Ed. pages 317–324 (1986), incorporated herein by reference. The particular surfactant is not believed to be critical to obtaining the anti-nonmicrobial malodor benefits of the present invention.

The skin cleansing deodorant compositions of the present invention can optionally contain, at their art-established levels, materials which are conventionally used in skin cleansing compositions, including antibacterial agents and fungicides, including those described above and also those described in U.S. Pat. No. 3,256,200, Reller et al., issued Jun. 14, 1966 (incorporated by reference herein); emollients, such as those described above, and also including mineral oils, paraffin wax having a melting point of from about 100° F. to about 170° F., fatty sorbitan esters (see U.S. Pat. No. 3,988,255, Selden, issued Oct. 26, 1976, incorporated by reference herein), lanolin and lanolin derivatives, esters such as isopropyl myristate and triglycerides such as coconut oil or hydrogenated tallow; free fatty acid, such as coconut oil fatty acid, preferably at levels up to about 10%, to improve the volume and quality (creaminess) of the lather produced by the compositions; and other ingredients such as perfumes, dyes, pigments, polymeric skin feel aids (such as cationic quaternized guar gum, e.g., Jaguar C-14-S, from Hoechst Celanese Corp.), humectants, thickening agents, preservatives, alkaline agents, propoxylated glycerol derivative skin conditioning agents, or other cosmetic adjuvants.

Skin cleansing compositions formulated as toilet soap bars generally comprise from about 50% to about 90% surfactant. Moisture is generally present at levels of from about 5% to about 20%. Skin cleansing compositions formulated as liquids generally comprise from about 10% to about 30% surfactant and from about 60% to about 90% water. Skin cleansing compositions formulated as pastes generally comprise from about 20% to about 60% surfactant and from about 30% to about 50% water. Pastes and liquids will also generally contain organic thickening agents such as natural gums and polymers.

Examples of soap-based toilet bar compositions are found in U.S. Pat. No. 3,567,749, Megson et al., issued Apr. 27, 1971, incorporated herein by reference. Examples of synthetic-based toilet bars which can be used in preparing compositions of the present invention are found in U.S. Pat. No. 2,987,484, Lundberg et al., issued Jun. 6, 1961, incorporated by reference herein. Other examples of soap/synthetic-based toilet bars are found in U.S. Pat. No. 3,070,547, Charfee, issued Dec. 25, 1962 and U.S. Pat. No. 3,376,229, Haas et al., issued Apr. 2, 1967, incorporated herein by reference. Examples of soap-based liquid cleansing compositions which can be used in preparing liquid compositions of the present invention are found in U.S. Pat. No. 4,310,433, Stiros, issued Jan. 12, 1982, incorporated herein by reference. Examples of synthetic-based liqutd cleansing compositions which can be used in preparing compositions of the present invention are found in U.S. Pat. No. 4,338,211, Stiros, issued Jun. 6, 1982, incorporated herein by reference. Paste compositions can be made by appropriate reduction in the levels of water in the compositions of U.S. Pat. Nos. 4,310,433 and 4,338,211, incorporated by reference herein. Examples of ultra mild skin cleansing compositions which can be used in preparing compositions of the present invention can be found in U.S. Pat. No. 4,673,525, Small et al., issued Jun. 16, 1987, incorporated by reference herein. Examples of skin cleansing mousse compositions with ethoxylated nonionic and wholly or partially esterified polyol nonionic surfactants and also having skin conditioning ingredients such as emollients and skin moisturizers can be found in U.S. Pat. No. 4,708,813, Snyder, issued Nov. 14, 1987, incorporated by reference herein. In addition to disclosing examples of skin cleansing compositions of the present invention, the above incorporated patents also disclose a variety of surfactants that can be used in the compositions of the present invention, including both soap-based and synthetic detergent-based surfactants. Skin cleansing deodorant compositions of the present invention are made by incorporating a 1,3-diketone deodorant agent in the above-identified compositions.

B. Laundry Product Compositions

Another aspect of the present invention involves laundry product compositions comprising a 1,3-diketone deodorant agent of the present invention and a laundry product carrier. Laundry product carriers can be in liquid, granular, or solid form and include liquid and granular detergents, and wash-added, rinse-added and dryer-added substrates which may also contain other ingredients, such as fabric conditioning and/or detergent ingredients. The laundry product compositions are formulated such that the 1,3-diketone deodorant agent either deodorizes the article of clothing during the laundry step and is washed or rinsed off (removal of odor), or is deposited on the article of clothing and remains to control nonmicrobial malodor (prevention of odor). The laundry product compositions of the present invention are believed to be especially beneficial for reducing nonmicrobial malodorous substances that become absorbed into the fabric.

Typically such laundry product compositions comprise from about 0,001% to about 20% of a 1,3 diketone deodorant agent. Laundry product compositions formulated for removal of odor preferably comprise from about 0.001% to about 1% of a 1,3-diketone deodorant agent, more preferably from about 0.005% to about 0.5%, more preferably still from about 0.01% to about 0.1%. Laundry product compositions formulated for prevention of odor preferably comprise from about 0.01% to about 10% of a 1,3-diketone deodorant agent, more preferably from about 0.1% to about 5%.

"Laundry product compositions", as used herein, include such compositions as liquid and granular laundry detergents, liquid and granular fabric conditioning and washer or dryer added substrates also containing fabric conditioners and/or detergent ingredients. Such compositions comprise a 1,3-diketone agents of the present invention and typically comprise, one or more of the following components.

Detersive Surfactants: The detergent compositions of this invention will contain organic surface-active agents ("surfactants") to provide the usual cleaning benefits associated with the use of such products.

Detersive surfactants useful herein include well-known synthetic anionic, nonionic, amphoteric and zwitterionic surfactants. Typical of these are the alkyl benzene sulfonates, alkyl- and alkylether sulfates, paraffin sulfonates, olefin sulfonates, amine oxides, alpha-sulfonates of fatty acids and of fatty acid esters, alkyl glycosides, ethoxylated alcohols and ethoxylated alkyl phenols, and the like, which are well-known from the detergency art. In general, such detersive surfactants contain an alkyl group in the $C_9-C_{18}$ range; the anionic detersive surfactants can be used in the form of their sodium, potassium or triethanolammonium salts. Standard texts such as the McCutcheon's Index contain detailed listings of such typical detersive surfactants. $C_{11}-C_{14}$ alkyl benzene sulfonates, $C_{12}-C_{18}$ paraffin-sulfonates, and $C_{11}-C_{18}$ alkyl sulfates and alkyl ether sulfates are especially preferred in the compositions of the present type.

Also useful herein are the water-soluble soaps, e.g., the common sodium and potassium coconut or tallow soaps well-known in the art. Unsaturated soaps such as alkyl soaps may be used, especially in liquid formulations. Saturated or unsaturated $C_9-C_{16}$ hydrocarbyl succinates are also effective.

Mixtures of the anionics, such as the alkylbenzene sulfonates, alkyl sulfates and paraffin sulfonates, with $C_9-C_{16}$ ethoxylated alcohol surfactants are preferred for through-the-wash cleansing of a broad spectrum of soils and stains from fabric.

Combinations of anionic, cationic and nonionic surfactants can generally be used. Such combinations, or combinations only of anionic and nonionic surfactants, are preferred for liquid detergent compositions. Such surfactants are often used in acid form and neutralized during preparation of the liquid detergent composition. Preferred anionic surfactants for liquid detergent compositions include linear alkyl benzene sulfonates, alkyl sulfates, and alkyl ethoxylated sulfates. Preferred nonionic surfactants include alkyl polyethoxylated alcohols.

Anionic surfactants are preferred for use as detergent surfactants in granular detergent compositions. Preferred anionic surfactants include linear alkyl benzene sulfonates and alkyl sulfates. Combinations of anionic and nonionic detersive surfactants are especially useful for granular detergent applications.

Detergent compositions will typically contain from about 10% to about 60% of a water-soluble detergent surfactant. Suitable surfactants and detergent compositions are described in U.S. Pat. No. 3,929,678, Laughlin et al., issued Dec. 30, 1975 and U.S. Pat. No. 4,294,710, Hardy et al., issued Oct. 13, 1981, both of which are incorporated herein by reference.

Conventional Builders: Builders used in the practice of this invention include various metal ion sequestering agents such as amine chelants and phosphonate chelants, such as diethylenetriamine pentaacetates, the alkylene amino phosphonates such as ethylenediamine tetraphosphonate, and the tripolyphosphate and "pyro" builders well known in the art. Importantly, various nonphosphorus builders can be used. Included among these by way of exemplification, but not limitation, are: 1-10 micron Zeolite A; 2,2'-oxodisuccinate; tartrate mono- and di-succinates; citrates; $C_8-C_{14}$ hydrocarbyl succinates; sodium carbonate; and mixtures thereof. Inorganic salts such as sodium sulfate can also be present. Lists of builders useful herein can be had by reference to U.S. Pat. No. 4,704,233, cited above.

Bleaches: Various well-known bleaching agents (especially fiber and fabric bleaches) are well known and may be used as components of the laundry product carriers. For laundry products, the sodium perborate mono- and tetra-hydrates are preferred, although the percarbonates and persulfates are also useful. Aqueous hypochlorite is also a routine additive in many laundering operations.

As noted previously, bleaching agents useful as components of the compositions of the present invention are limited to those which are compatible with the 1,3-diketone compound in the composition.

Detersive Adjuncts: The compositions herein can contain various ingredients which aid in their cleaning performance. For example, it is preferred that the laundry compositions herein also contain enzymes to enhance their through-the-wash cleaning performance on a variety of soils and stains. Amylase and protease enzymes suitable for use in detergents are well-known in the art and in commercially available liquid and granular detergents. Commercial detersive enzymes (preferably a mixture of amylase and protease) are typically used at levels of 0,001% to 2%, and higher, in the present compositions.

Moreover, the compositions herein can contain, in addition to ingredients already mentioned, various other optional ingredients typically used in commercial products to provide aesthetic or additional product performance benefits. Typical ingredients include pH regulants, perfumes, dyes, bleaches, optical brighteners, polyester soil release agents, hydrotropes and gel-control agents, freeze-thaw stabilizers, bacteriocides, preservatives, suds control agents, bleach activators and the like. Fabric softeners, especially clays and mixtures of clays with various amines and quaternary ammonium compounds, can all be used in the compositions. Such matters are well-known from the patent literature and in commercial practice.

The compositions herein are prepared using conventional techniques, well-known to the formulator of commercial detergent and bleach products.

Fabric conditioning agents, when present in the laundry product compositions, typically comprise between about 1% and about 35% of the composition, preferably between about 6% and about 25%. The particular fabric conditioning agent utilized is not believed to be critical to the present invention, and any of those fabric conditioning agents known in the art are believed to be applicable. These include, for example, quaternary ammonium fabric conditioners, such as those disclosed in U.S. Pat. No. 3,936,537, Baskerville et al., issued Feb. 3, 1976, tertiary amines, such as those disclosed in British Patent 1,514,276, Kenyon, published Jun. 14, 1978, amine-anion ion-pair complexes including those disclosed in British Patents 1,077,103 and 1,077,104, assigned to Bayer, published Jul. 26, 1977, and U.S. patent application Ser. No. 153,172, Caswell, filed Feb. 8, 1988, and smectite-type clay softening systems, such as those described in U.S. Pat. No. 4,062,647, Storn et al., issued Dec. 13, 1977, British Patent 1,483,627, assigned to Procter & Gamble, published Aug. 24, 1977.

Aqueous dispersions useful for direct application to articles of clothing in an aerosol-form comprise a 1,3-diketone deodorant agent; from about 0.1% to 10% water; from about 0.01% to about 5% of a suitable organic solvent; the balance being a suitable propellant. Examples of such propellants are the chlorinated, fluorinated and chlorofluorinated lower molecular weight hydrocarbons. Nitrous oxide, carbon dioxide, isobutane and propane may also be used as propellant gases. These propellants are used at a level sufficient to expel the contents of the container. Suitable organic materials useful as the solvent or a part of a solvent system are as follows: propylene glycol, polyethylene glycol (M.W. 200–600), polypropylene glycol (M.W. 425–2025), glycerine, sorbitol esters, 1,2,6-hexanetriol, deithyl tartrate, butanediol, and mixtures thereof. The balance of the composition comprises a liquid carrier, preferably the carrier is water or a mixture of water and monohydric alcohols.

Liquid fabric-treatment compositions can be prepared by mixing the 1,3-diketone deodorant agent into a solvent, alone or with other components.

The deodorant agents of the present invention can be added to granular carriers by admixing the deodorant agent in solution with other of the compositions ingredients prior to the time when they are spray dried, and then spray drying said mixture in a conventional manner. Alternatively, granular or powder laundry product compositions can be made by dry blending the deodorant agents with other of the composition ingredients.

C. Fabric Treatment Compositions

Another aspect of the present invention involves fabric treatment compositions comprising 1,3-diketone agents of the present invention for deposition onto articles of clothing or fabric worn in the vicinity of the skin, and a fabric treatment carrier. "A fabric treatment carrier," as used herein, typically comprises one or more of the following components: optical brighteners, surfactants (preferably nonionic or anionic) or organic esters. The fabric treatment compositions can, it is believed, inhibit or reduce the formation of nonmicrobial malodor due to axilla or crotch area sweat that has been absorbed by said clothing. Fabric treatment carriers include liquid and granular fabric conditioning compositions, and stain and/or odor removing compositions formulated such that the 1,3-diketone deodorant agent is deposited on articles of clothing prior to washing or drying of said articles, or prior to use or wearing of said articles, such that the deodorant agent is deposited upon an article and remains deposited at least during the initial period when the article is worn or used. Typically, such compositions will contain from about 0.01% to about 20% of the 1,3-diketone compounds of the present invention, preferably from about 0.1% to about 10%.

D. Catamenials and Diapers

Another aspect of the present invention involves compositions to control nonmicrobial malodor comprising an absorbent substrate carrier on a catamenial or diaper product (including adult incontinent) and a deodorant agent of the present invention. "Absorbent substrate carrier" as used herein, means an absorbent layer or core of material comprising wood pulp fibers, cotton fibers, polyester fibers or other liquid or solid absorbent materials. Deodorant compositions containing the deodorant agent of the present invention for use to control urine-based and menstrual fluid-based malodor can include, but are not limited to, catamenial products such as sanitary napkins and panty liners and infant and adult diapers. Another aspect of the present invention provides deodorant and deodorant/anti-septic compositions comprising the deodorant agent of the present invention and perfumes or antimicrobial agents for use in urinals and toilets, catamenials, and bedding.

E. Methods

The present invention also provides methods for controlling or inhibition of malodor, preferably malodor of human perspiration, comprising topically applying a safe and effective amount of one or more of the 1,3-diketone compositions of the present invention to areas of the skin subject to secretion of both apocrine and eccrine sweat, i.e., the axilla and crotch areas of the body.

Methods of using the composition of the present invention to control nonmicrobial malodor comprise topically applying compositions of the present invention; the compositions are preferably applied such that from about 0.002 mg to about 4.0 mg, preferably from about 0.01 mg to about 1.0 mg, of the deodorant agent is applied per one square centimeter of skin.

Additionally, the present invention provides methods of controlling nonmicrobial malodor in articles of clothing and fabric by depositing a safe and effective amount of a 1,3-diketone agent of the present invention to an area of the article of clothing of fabric. Preferably the deodorant composition is applied to the article of clothing at areas which typically come in contact with both eccrine gland and apocrine gland perspiration when worn, particularly the axilla and crotch regions. Preferably, from about 0.002 to about 4.0, preferably from about 0.01 to about 1.0, milligrams of the 1,3-diketone deodorant agent is deposited per one square centimeter of the article of clothing or fabric.

The present invention also provide methods of contacting an article of clothing or fabric with an aqueous detergent solution comprising from about 0.1% to about 2% by weight of a detergent composition of the present invention. Fabrics to be laundered are agitated, preferably in an automatic washing machine, in these solutions to effect cleaning, stain removal, fabric care benefits, and malodor control. Compositions can also be applied to articles of clothing or fabric by tumbling said articles with the composition in an automatic laundry dryer.

The present invention also provides methods of controlling malodor comprising contacting or depositing a 1,3-diketone deodorant agents of the present invention to catamenial products that come into contact with urine, feces and/or menstrual fluid. Preferred methods further comprising contacting or depositing the deodorant agents to catamenial products comprising an absorbent substrate carrier.

The following non-limiting examples illustrate compositions of the present invention.

Compositions for topical administration are prepared as follows:

EXAMPLE I

| | |
|---|---|
| Dipropylene glycol | 28% |
| Sodium stearate | 6% |
| Propylene glycol (3) myristyl ester | 21% |
| Cyclodecamethylpentasiloxane | 19% |
| Ethanol | 24.7% |
| 5-chloro-2-(2,4-dichlorophenoxy)-phenol | 0.3% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

EXAMPLE II

| | |
|---|---|
| Cyclodecamethylpentasiloxane | 39% |
| Dipropylene glycol | 25% |
| Propylene glycol (3) myristyl ester | 20% |
| Perfume | 1.4% |
| Ethanol | 13.6% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

EXAMPLE III

| | |
|---|---|
| Propylene carbonate | 8.7% |
| Propylene glycol | 4.3% |
| Dipropylene glycol | 36% |
| PEG-6 | 10% |
| Propylene glycol (3) myristyl ester | 10% |
| Millithix 925* | 4.9% |
| Ethanol | 24.8% |
| 5-chloro-2-(2,4-dichlorophenoxy)-phenol | 0.3% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

EXAMPLE IV

| | |
|---|---|
| Ethyl acetate | 30.7% |
| Cyclodecamethylpentasiloxane | 68% |
| 5-chloro-2-(2,4-dichlorophenoxy)-phenol | 0.3% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

EXAMPLE V

| | |
|---|---|
| Ethyl acetate | 30.7% |
| Cyclodecamethylpentasiloxane | 68% |
| 5-chloro-2-(2,4-dichlorophenoxy)-phenol | 0.3% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

EXAMPLE VI

| | |
|---|---|
| Acetone | 30.7% |
| Cyclodecamethylpentasiloxane | 68% |
| 5-chloro-2-(2,4-dichlorophenoxy)-phenol | 0.3% |
| Meldrum's acid | 1.0% |
| | 100.0% |

Meldrum's acid is mixed with the other above-listed ingredients for use as a deodorant using methods known in the art. Dimedone or other 1,3-diketone compounds useful in the composition of the present invention may be substituted for the above 1,3-diketone compound in the composition.

The purpose of this example is to exemplify the effectiveness of the present invention for reducing or inhibiting nonmicrobial malodor.

EXAMPLE VII

Additional granular detergent compositions of the present invention comprise the following ingredients:

| Ingredient | Percent (wt) |
|---|---|
| Sodium 12.3 linear alkyl benzene sulfonate | 15.8 |
| Sodium $C_{14}$–$C_{15}$ alkyl sulfate | 6.8 |
| $C_{12}$–$C_{13}$ alcohol ethoxylate (EO 6) | 0.5 |
| Sodium tripolyphosphate | 6.8 |
| Sodium pyrophosphate | 13.1 |
| Sodium acid pyrophosphate | 12.4 |
| Sodium silicate (1.6 ratio $Na_2O/SiO_2$) | 7.6 |
| Polyethylene glycol 8000 | 0.6 |
| Sodium polyacrylate (MW 4500) | 3.4 |
| Protease enzyme* | 1.8 |
| Sodium perborate tetrahydrate | 1.9 |
| Sodium sulfate | 14.4 |
| 2,2-dimethyl-1,3-dioxane-4,6-dione | .05 |
| Balance (including water, brightener, perfume, suds suppressor) | 14.85 |
| | 100.0 |

Aqueous crutcher mixes of the detergent compositions are prepared and spray-dried, except for the, sodium acid pyrophosphate, enzyme, and perfume, which are admixed, so that they contain the above ingredients at the levels shown.

EXAMPLE VIII

An additional granular detergent composition for household laundry use is as follows:

| Component | Amount(%) |
|---|---|
| Sodium $C_{14}$–$C_{15}$ alkylsulfate | 13.3 |

| Component | Amount(%) |
|---|---|
| Sodium C₁₃ linear alkyl benzene sulfonate | 5.7 |
| C₁₂-C₁₃ alkylpolyethoxylate (6.5) | 1.0 |
| Sodium toluene sulfonate | 1.0 |
| *TMS/TDS, sodium salt, 86/14 weight ratio of TMS:TDS | 25.0 |
| Sodium N-hydroxyethylethylenediaminetriacetate | 2.0 |
| Sodium polyacrylate (Avg. M.W. approx. 5000) | 2.0 |
| Sodium carbonate | 20.3 |
| Sodium silicate | 5.8 |
| Polyethylene glycol (Avg. M.W. approx. 8000) | 1.0 |
| 2,2-dimethyl-1,3-dioxane-4,6-dione | 0.05 |
| Sodium sulfate, water and miscellaneous** | 22.85 |
| | 100.0 |

*TMS/TDS - mixture of tartrate monosuccinate and tartrate disuccinate in a TMS to TDS weight ratio of 85/15 sodium salt form
**includes perfume, buffers, colorants, opacifiers and the like The components are added together with continuous mixing with sufficient extra water (about 40% total) to form an aqueous slurry which is then spray dried to form the composition.

EXAMPLE IX

An additional liquid detergent composition for household laundry use is as follows:

| Component | Amount(%) |
|---|---|
| Potassium C₁₄-C₁₅ alkyl polyethoxy (2.5) sulfate | 8.3 |
| C₁₂-C₁₄ alkyl dimethyl amine oxide | 3.3 |
| Potassium toluene sulfonate | 5.0 |
| Monoethanolamine | 2.3 |
| TMS/TDS triethanolamine salt, 85/15 TMS/TDS | 15.0 |
| Potassium salt of 1,2-dihydroxy-3,5-disulfobenzene | 1.5 |
| Potassium polyacrylate (avg. M.W. approx. 9000) | 1.5 |
| 2,2-dimethyl-1,3-dioxane-4,6-dione | 0.01 |
| Water and miscellaneous* | 63.09 |
| | 100.0 |

*includes perfume, buffers, colorants, opacifiers and the like

The components are added together with continuous mixing to form the composition.

EXAMPLE X

| Fabric Conditioning Agent | |
|---|---|
| Component | Amount(%) |
| Ditallow di-methyl ammonium chloride (DTDMAC) | 3.7 |
| Methyl-1-tallow amido ethyl 2-tallow imidazoline | 3.7 |
| 2,2-dimethyl-1,3-dioxane-4,6-dione | 0.1 |
| Water and miscellaneous | 92.5 |
| | 100.0 |

The disclosed 1,3-diketone compounds control a variety of other malodors in addition to human perspiration. Such other malodors include, but are not limited to, environmental odors and chemical odors. In addition, the disclosed 1,3-diketone compounds control negative odors generated by or deposited on various porous and nonporous surfaces including, but not limited to, plastics, wood, hair, glass, porcelain, fabric, fibers of varying compositions, foods, and beverages. Such negative odors may be controlled by applying the 1,3-diketone compound to said surfaces before, during or after the odor has been generated, or by incorporating the 1,3-diketone compound into these surfaces during manufacture. As used herein, "control odors, malodors, or negative odors" means preventing, retarding, or reversing such odor formation. As used herein, "negative odor or malodor" means an odor emanating from a particular surface or manufacture which is undesirable.

Applicants have further determined that the disclosed 1,3-diketone compounds, preferably 2,2-dimethyl-1,3-dioxane-4,6-dione, are highly effective in controlling malodors associated with a laundry cleaning product. Though the mechanism upon which this deodorization is based is unknown, it is believed to be something beyond an interaction with vitamin Be reactions. Such a surprising application is extremely useful in laundry product compositions which do not comprise a perfume, as these compositions often have negative odors emanating from their substituents including, but not limited to, solvents, enzymes, surfactants, or contaminants. In addition to deodorizing these negative odors, the 1,3-diketone deodorant agent enhances positive odors in the laundry product, such as perfumes.

The present invention further relates to compositions effective for controlling malodors associated with chemical formulations of laundry cleaning products. Laundry product compositions with reduced negative laundry product odor comprise from about 0.001% to about 20% of a 1,3-diketone compound.

The present invention further relates to methods effective for controlling malodors associated with chemical formulations of laundry cleaning products. Methods for controlling negative laundry product odors comprise inclusion of from about 0.001% to about 20% of a 1,3-diketone compound in a laundry product composition.

What is claimed is:

1. A deodorant composition for preventing the formation of malodor from perspiration comprising:

a) from about 0.01% to about 20% of a 1,3-diketone compound having the general formula:

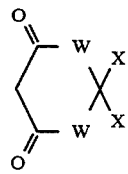

wherein each W is independently selected from the group consisting of O, S and (CH₂)ₙ, wherein n=1–3;

and each X is independently selected from the group consisting of hydrogen, halogen, substituted and unsubstituted alkyl having from about 1 to about 5 carbon atoms, or two X moieties are covalently bonded to form a structure selected from the group consisting of substituted and unsubstituted alkyl, and aryl wherein the aryl is selected from the group consisting of substituted phenyl, substituted naphthyl, unsubstituted phenyl and unsubstituted naphthyl, and wherein the substituents of any substituted alkyls, substituted phenyl and substituted naphthyl are independently selected from the group consisting of halogen, alkyl, hydroxy, amino, phenyl, naphthyl, carboxylate, nitro, —CF₃ and —OR wherein R is an unsubstituted alkyl having from about 1 to about 3 carbon atoms; and b) a topical carrier comprising an emollient.

2. The composition of claim 1, wherein W is independently selected from the group consisting of O and ($CH_2$)$_n$, wherein n=1−3; and X is independently selected from the group consisting of hydrogen and substituted and unsubstituted alkyl having form about 1 to about 5 carbon atoms.

3. The composition of claim 2, wherein at least one W is 0; and X is independently selected from the group consisting of hydrogen and unsubstituted and substituted alkanyl.

4. The composition of claim 2, wherein both W are $CH_2$; and X is independently selected from the group consisting of hydrogen, methyl and ethyl.

5. The composition of claim 1, wherein said 1,3-diketone compound is selected from the group consisting of spiro-(4,5)-6,10-dioxa-7,9-dioxodecane and spiro-(5.5)-1,5-dioxa-2,4-dioxoundecane.

6. The composition of claim 4, wherein said 1,3-diketone compound is 2,2-dimethyl-1,3-dioxane-4,6-dione.

7. The composition of any of claims 1, 2, 4 or 6 further comprising from about 0.1% to about 10% of an antimicrobial agent selected from the group consisting of cetyltrimethyl ammonium bromide, cetyl pyridinium chloride, benzethonium chloride, diisobutyl phenoxy ethoxy ethyl dimethyl benzyl ammonium chloride, sodium N-lauryl-sarcosine, sodium N-polymethyl sarcosine, lauroyl sarcosine, N-myristoyl glycine, potassium N-lauroyl sarcosine, stearyl trimethyl ammonium chloride, 2,4,4'-trichloro-2'hydroxydiphenyl ether, zinc pyrithione, sodium bicarbonate, 2,2'-methylene-bis(3,4,6-trichlorophenol), zinc phenolsulfonate, 2,2'-thiobis(4,6-dichlorphenol), p-chloro-m-xylenol, dichloro-m-xylenol and a diaminoalkyl amide.

8. A method for preventing the formation of malodor from perspiration comprising topically applying to skin in the axilla or crotch region, a safe and effective amount of the composition of any of claims 1, 2, 4, 5 or 6.

* * * * *

UNITED STATES PATENT AND TRADEMARK OFFICE
CERTIFICATE OF CORRECTION

PATENT NO. : 5,441,727
DATED : August 15, 1995
INVENTOR(S) : Ranjit Chatterjee et al.

It is certified that error appears in the above-indentified patent and that said Letters Patent is hereby corrected as shown below:

Column 3, line 29, "Z" should read --2--.
Column 5, line 3, "g" should read --9--.
Column 5, line 30, "Miss." should read --Mo--.
Column 7, line 52, "theology" should read --rheology--.
Column 8, line 53, "Gell All-De" should read --Gell All-D®--.
Column 8, line 55, "Millithixs" should read --Millithix®--.

Column 10, line 28, "

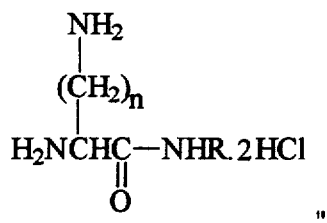

"

should read --As used herein "diaminolkyl amide" means an antimicrobial agent having the general structure

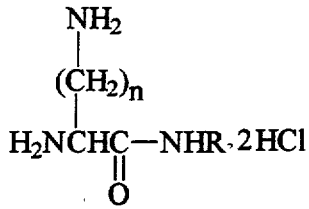

wherein R is a $C_{12}$-$C_{18}$ alkyl and n is an integer selected from the group consisting of 2, 3 and 4--.

UNITED STATES PATENT AND TRADEMARK OFFICE
CERTIFICATE OF CORRECTION

PATENT NO. : 5,441,727
DATED : August 15, 1995
INVENTOR(S) : Ranjit Chatterjee et al.

It is certified that error appears in the above-indentified patent and that said Letters Patent is hereby corrected as shown below:

Column 11, line 18, ")5%" should read --5%--.
Column 16, line 35, "0,001%" should read --0.001%--.
Column 16, line 68, "U.S. patent application Ser. No. 153,172" should read --U.S. Serial No. 153,172--.

Column 20, line 55, text omitted; insert --pH 1% aqueous solution at 20°C        9.2
                                            * Reported in Anson units per gram--.
Column 22, line 9, "Be" should read --$B_6$--.

Signed and Sealed this

Eighth Day of April, 1997

Attest:

BRUCE LEHMAN

*Attesting Officer*    *Commissioner of Patents and Trademarks*